United States Patent
Omori et al.

(10) Patent No.: US 6,344,559 B1
(45) Date of Patent: Feb. 5, 2002

(54) PROCESS FOR PRODUCING QUINAZOLINE DERIVATIVES

(75) Inventors: Hiroki Omori, Amagasaki; Shunsuke Goto, Osaka; Hiroyuki Tsuboi, Neyagawa; Masayasu Fukagawa, Toyama; Kooji Kagara, Mino, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/380,609

(22) PCT Filed: Mar. 17, 1998

(86) PCT No.: PCT/JP98/01111

§ 371 Date: Oct. 13, 1999

§ 102(e) Date: Oct. 13, 1999

(87) PCT Pub. No.: WO98/41514

PCT Pub. Date: Sep. 24, 1998

(30) Foreign Application Priority Data

Mar. 17, 1997 (JP) .............................. 9-062617

(51) Int. Cl.⁷ ........................................... C07D 239/96
(52) U.S. Cl. ..................................................... 544/285
(58) Field of Search ......................................... 544/285

(56) References Cited

U.S. PATENT DOCUMENTS

| | | | |
|---|---|---|---|
| 5,756,738 A | 5/1998 | Nishii et al. | 544/283 |
| 5,994,542 A | 11/1999 | Asada et al. | 544/283 |

*Primary Examiner*—John M. Ford
*Assistant Examiner*—Venkataraman Balasubramanian

(74) *Attorney, Agent, or Firm*—Oblon, Spivak, McClelland, Maier & Neustadt, P.C.

(57) ABSTRACT

This invention provides an industrially useful process for producing a quinazoline derivative (I) of the general formula:

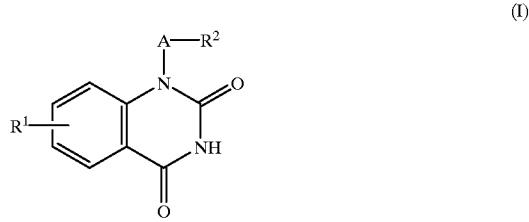

[wherein $R^1$ is hydrogen or halogen; $R^2$ is carboxy or protected carboxy; A is lower alkylene] or its salt on a commercial scale which comprises reacting a compound of the general formula:

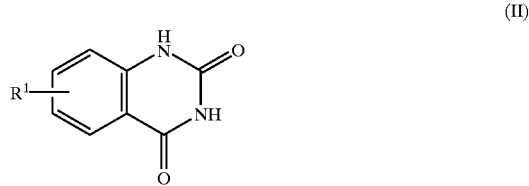

[wherein $R^1$ is hydrogen or halogen] or its salt with a silylating agent and then with a compound of the general formula:

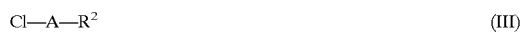

[wherein R2 is carboxy or protected carboxy; A is lower alkylene] or its salt, optionally followed by desilylation.

7 Claims, No Drawings

PROCESS FOR PRODUCING QUINAZOLINE DERIVATIVES

TECHNICAL FIELD

This invention relates to a novel process for producing the under-mentioned quinazoline derivative (I) of value as a starting compound for the quinazoline derivative described in Japanese Kokai Tokkyo Koho S62-96476, and finds application in pharmaceutical industry.

BACKGROUND ART

This invention provides a novel and industrially improved process for producing said quinazoline derivative (I).

DISCLOSURE OF INVENTION

This invention relates to a process for producing a quinazoline derivative of the following general formula or a salt thereof:

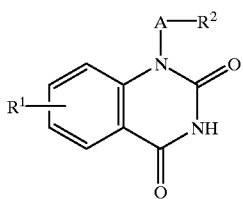

(I)

[wherein $R^1$ is hydrogen or halogen; $R^2$ is carboxy or protected carboxy; A is lower alkylene]

The present process for producing quinazoline derivative (I) or its salt is as schematically illustrated below.

Process

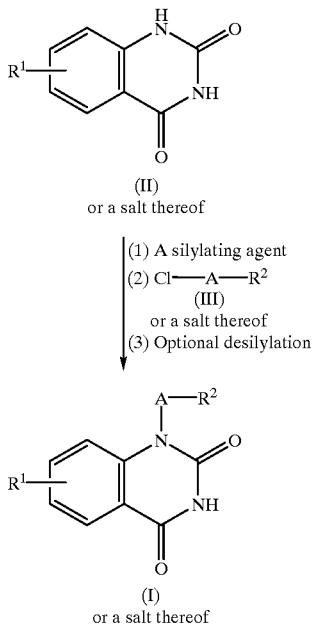

[wherein $R^1$, $R^2$ and A are as defined above]

The inventors of this invention explored in earnest for a novel production technology for quinazoline derivative (I) and found that by reacting compound (II) with a silylating agent and then with compound (III), optionally followed by desilylation, quinazoline derivative (I) can be produced at low cost, expediently, safely, and in good yield. This invention has been developed on the basis of the above finding.

The salt of quinazoline derivative (I) according to this invention includes salts with bases, for example salts with inorganic bases, e.g. salts with alkali metals such as lithium, sodium, potassium, etc., salts with alkaline earth metals such as calcium, magnesium, etc. and ammonium salts, salts with organic bases, e.g. salts with organic amines such as triethylamine, pyridine, picoline, ethanolamine, triethanolamine, dicyclohexylamine, N,N'-dibenzylethylenediamine, etc., and acid addition salts e.g. inorganic acid addition salts such as hydrochloride, hydrobromide, sulfate, phosphate, etc. and organic acid addition salts such as formate, acetate, trifluoroacetate, maleate, tartrate, methanesulfonate, benzenesulfonate and toluenesulfonate, among others.

The various definitions given in the foregoing and following disclosures which fall within the scope of this invention are now explained and the relevant subgeneric and specific examples and comments are also given below.

The term "lower" as used throughout this specification means 1~6 carbon atoms unless otherwise specified.

Suitable examples of "halogen" includes fluorine, chlorine, bromine and iodine, for instance.

Suitable examples of "substituted silyl" includes mono(or di or tri)-substituted silyl.

The suitable substituent or substituents on "mono (or di or tri)-substituted silyl" include but are not limited to lower alkyl, lower alkenyl, aryl, and ar(lower)alkyl optionally having one or more suitable substituents.

Suitable examples of said "lower alkyl" and suitable examples of the "lower alkyl moiety" of said "ar (lower) alkyl optionally having one or more suitable substituents" include straight-chain or branched-chain alkyl groups such as methyl, ethyl, propyl, isopropyl, butyl isobutyl, tert-butyl, pentyl, hexyl, etc.

Suitable examples of said "lower alkenyl" include straight-chain or branched-chain alkenyl groups of 2~6 carbon atoms, such as vinyl, allyl, isopropenyl, 1-, 2- or 3-butenyl, 1-, 2-, 3- or 4-pentenyl, and 1-, 2-, 3-, 4- or 5-hexenyl, among others.

Suitable examples of said "aryl" and suitable examples of the "aryl moiety" of said "ar(lower)alkyl optionally having 1 or more suitable substituents" include phenyl and naphthyl, among others.

The "suitable substituents" mentioned for "ar(lower)alkyl optionally having 1 or more suitable substituents" include but are not limited to mono(or di or tri)-halo(lower)alkyl groups (e.g. chloromethyl, bromomethyl, chloropropyl, 1,2-dichloroethyl, 1,2-dibromoethyl, 2,2-dichloroethyl, trifluoromethyl, 1,2,2-trichloroethyl, etc.), lower alkoxy groups (e.g. methoxy, ethoxy, propoxy, isopropoxy, butoxy, isobutoxy, pentyloxy, isopentyloxy, hexyloxy, etc.), halogen atoms (e.g. fluorine, chlorine, bromine and iodine), and lower alkyl groups (e.g. methyl, ethyl, propyl, isopropyl, butyl, isobutyl, t-butyl, pentyl, hexyl, etc.).

Suitable examples of "protected carboxy" include but are not limited to esterified carboxy, such as lower alkoxycarbonyl (e.g. methoxycarbonyl, ethoxycarbonyl, propoxycarbonyl, isopropoxycarbonyl, butoxycarbonyl, t-butoxycarbonyl, etc. ) and mono(or di or tri)-phenyl(lower) alkoxycarbonyl optionally having nitro (e.g. benzyloxycarbonyl, 4-nitrobenzyloxycarbonyl, phenethyloxycarbonyl, benzhydryloxycarbonyl, trityloxycarbonyl, etc.). The more preferred, among them, are $C_1$–$C_4$ alkoxycarbonyl groups and the most preferred species is ethoxycarbonyl.

Suitable examples of said "lower alkylene" include both straight-chain and branched chain groups such as, for example, methylene, ethylene, trimethylene, tetramethylene, pentamethylene, hexamethylene, methylmethylene, ethylethylene and propylene. The more preferred, among them, are $C_1$–$C_4$ alkylene groups and the most preferred species is methylene.

The process for producing quinazoline derivative (I) according to this invention is now described in detail.

Process

Quinazoline derivative (I) or its salt can be produced by reacting compound (II) or a salt thereof with a silylating agent and further with compound (III) or a salt thereof, optionally followed by desilylation. As suitable salts of compound (II), salts with the same acids as mentioned for compound (I) can be mentioned. Suitable salts of compound (III) further include salts with the same bases as mentioned for compound (I).

The silylating agent which can be used with advantage in this invention includes but is not limited to hexamethyldisilazane, trimethylchlorosilane, N,O-bis(trimethylsilyl)acetamide, hexamethyldisiloxane, N-trimethylsilylacetamide, N-methyl-N-trimethylsilylacetamide, N-trimethylsilyldimethylamine, N-trimethylsilyldiethylamine, N-trimethylsilyl-t-butylamine and N-trimethylsilylimidazole.

The reaction with the silylating agent is generally carried out in a routine solvent which does not interfere with reaction, for example toluene, tetrahydrofuran, dioxane, dichloromethane or the like. The reaction temperature is not particularly restricted but this reaction is generally conducted under cooling through heating.

The reaction with compound (III) or a salt thereof is preferably carried out in the presence of a catalyst.

The catalyst suited for this reaction includes bromides [e.g. compounds of the formula Br—Y—$R^3$ [wherein $R^3$ represents carboxy or protected carboxy (preferably esterified carboxy, more preferably lower alkoxycarbonyl, most preferably ethoxycarbonyl) and Y represents lower alkylene (preferably $C_1$–$C_4$ alkylene, most preferably methylene)], inclusive of salts thereof, compounds of the formula Br—$R^4$ [wherein $R^4$ represents substituted or unsubstituted silyl (preferably tri-substituted silyl, more preferably tri(lower)-alkylsilyl, most preferably trimethylsilyl)], inclusive of salts thereof, and compounds of the formula $MX^1$ [wherein M represents an alkali metal (preferably sodium or lithium) and $X^1$ represents bromo or iodo (preferably bromo)], among others]. The preferred catalyst is a compound of the formula Br—Y—$R^3$ or a salt thereof.

The amount of the catalyst based on each mole of compound (II) or its salt is preferably about 0.1~0.5 mole, more preferably about 0.1~0.4 mole.

This reaction is carried out in the presence of a routine solvent which does not interfere with the reaction or optionally in the absence of a solvent. Preferably, however, the reaction is conducted in a solvent having a large dielectric constant (preferably, dielectric constant $\in \geq 5$) (such as propylene carbonate, nitrobenzene, dichlorobenzene, etc.), and the most preferred solvent is propylene carbonate.

The reaction temperature is not particularly restricted but this reaction is carried out under warming or heating, preferably at a temperature not below about 80° C., more preferably about 90~160° C., and most preferably about 100~150° C.

When the reaction product is to be desilylated where necessary, this desilyation reaction can be carried out in the routine manner, for example by hydrolysis or alcoholysis.

The production of quinazoline derivative (I) or a salt thereof from compound (II) or a salt thereof in accordance with this invention can be carried out in a continuous mode without an intermediate isolation step.

The following preparation and examples illustrate this invention in further detail.

Preparation 1

In 4-chloroanthranilic acid (40 g) were dissolved 24% aqueous sodium hydroxide (42.74 g), water (280 ml) and sodium cyanate (90% content) (25.26 g) with stirring. The resulting solution was adjusted to pH 6.5~6.9 with concentrated hydrochloric acid at an internal temperature of 28~32° C. and the reaction was carried out under the same conditions for 3.5 hours. To this reaction mixture was added methanol (80 ml), and after the whole mixture was warmed to 55~60° C., 24% aqueous sodium hydroxide (97.13 g) was added dropwise over about one hour at the same temperature. After completion of dropwise addition, the reaction was continued at the same temperature for another one hour.

This reaction mixture was cooled to 0~20° C. and stirred at this temperature for 1 hour. The crystals separating out were collected by filtration. To the wet crystal crop thus harvested was added water (280 ml)-methanol (280 ml), followed by addition of concentrated hydrochloric acid (26.8 g) dropwise at an internal temperature of 30~35° C. over about 30 minutes. The reaction was then conducted at the same temperature for 2 hours. The resulting crystals were collected by filtration, washed with water and dried to provide 7-chloro-2,4-dioxo-1,2,3,4-tetrahydroquinazoline (43.58 g).

IR (Nujol): 3310, 1760, 1700, 1630, 750 $cm^{-1}$

NMR (DMSO-$d_6$, δ): 7.17–7.24 (2H, m), 7.88 (1H, d, J=7 Hz), 11.3 (2H, broad s)

EXAMPLE 1

To a mixed suspension of 7-chloro-2,4-dioxo-1,2,3,4-tetrahydroquinazoline (20 g) and hexamethyldisilazane (16.42 g) in toluene (60 ml) was added sulfuric acid (0.80 g) dropwise and the silylation reaction was carried out at an internal temperature of 110~120° C. for 6 hours. After completion of silylation, the toluene was distilled off to recover a concentrate containing 7-chloro-2,4-bis(trimethylsilyloxy)quinazoline. To this concentrate were added propylene carbonate (40 ml), ethyl chloroacetate (13.72 g) and ethyl bromoacetate (3.40 g), and the reaction was carried out at an internal temperature of 125~140° C. for 6 hours. After completion of reaction, the reaction mixture was cooled to an internal temperature of ≦70° C. and ethyl acetate (80 ml) was added. Then, methanol (60 ml) was added dropwise over 30 minuets. After completion of dropwise addition, the mixture was cooled to ≦20° C. and stirred for 1 hour. The resulting crystal crop was harvested by filtration, washed serially with methanol (40 ml) and water (100 ml) and dried to provide ethyl 2-(7-chloro-2,4-dioxo-1,2,3,4-tetrahydroquinazolin-1-yl)acetate (28.16 g) as white crystals.

IR (Nujol): 3180, 3050, 1750, 1700, 1610, 1230, 1210, 850 $cm^{-1}$

NMR (DMSO-$d_6$, δ): 1.24 (3H, t, J=7 Hz), 4.20 (2H, q, J=7 Hz), 4.93 (2H, s), 7.34 (1H, dd, J=8.5 Hz, 2 Hz), 7.60 (1H, d, J=2 Hz), 8.04 (1H, d, J=8.5 Hz), 11.8 (1H, broad s)

EXAMPLE 2

As in Example 1, 7-chloro-2,4-dioxo-1,2,3,4-tetrahydroquinazoline (20 g) was silylated and the toluene was distilled off to give a concentrate containing 7-chloro- 2,4-bis(trimethylsilyloxy)quinazoline. To this concentrate were added propylene carbonate (40 ml), ethyl chloroacetate (16.21 g) and bromotrimethylsilane (3.11 g), and the reaction was carried out at an internal temperature of 125~140° C. for 8 hours. This reaction mixture was cooled to ≦70° C. and worked up as in Example 1 to provide ethyl 2-(7-chloro-2,4-dioxo-1,2,3,4-tetrahydroquinazolin-1-yl)acetate (27.90 g).

EXAMPLE 3

As in Example 1, 7-chloro-2,4-dioxo-1,2,3,4-tetrahydroquinazoline (20 g) was silylated and the toluene was distilled off to give a concentrate containing 7-chloro-2,4-bis(trimethylsilyloxy)quinazoline. To this concentrate were added propylene carbonate (40 ml), ethyl chloroacetate (16.21 g) and sodium bromide (2.09 g), and the reaction was carried out at an internal temperature of 125~140° C. for 10 hours. This reaction mixture was cooled to ≦70° C. and worked up as in Example 1 to provide ethyl 2-(7-chloro-2,4-dioxo-1,2,3,4-tetrahydroquinazolin-1-yl)acetate (27.02 g).

EXAMPLE 4

7-Chloro-2,4-dioxo-1,2,3,4-tetrahydroquinazoline (10 g) was treated as in Example 1 to give a concentrate containing 7-chloro-2,4-bis(trimethylsilyloxy)quinazoline. To this concentrate was added ethyl chloroacetate (20 ml), and the reaction was carried out at an internal temperature of 140~150° C. for 29 hours. This reaction mixture was cooled to ≦70° C., and after addition of ethyl acetate (20 ml), a solvent mixture of methanol (30 ml) and ethyl acetate (20 ml) was added dropwise over about 30 minutes. After completion of dropwise addition, the mixture was worked up as in Example 1 to provide ethyl 2-(7-chloro-2,4-dioxo-1,2,3,4-tetrahydroquinazolin-1-yl)acetate (13.60 g).

EXAMPLE 5

7-Chloro-2,4-dioxo-1,2,3,4-tetrahydroquinazoline (10 g) was treated as in Example 1 to give a concentrate containing 7-chloro-2,4-bis(trimethylsilyloxy)quinazoline. To this concentrate were added ethyl chloroacetate (21.70 g) and ethyl bromoacetate (1.70 g), and the reaction was carried out at an internal temperature of 130~140° C. for 13 hours. This reaction mixture was cooled to ≦70° C. and worked up as in Example 4 to provide ethyl 2-(7-chloro-2,4-dioxo-1,2,3,4-tetrahydroquinazolin-1-yl)acetate (13.76 g).

EXAMPLE 6

7-Chloro-2,4-dioxo-1,2,3,4-tetrahydroquinazoline (10 g) was treated as in Example 1 to give a concentrate containing 7-chloro-2,4-bis(trimethylsilyloxy)quinazoline. To this concentrate was added an oil prepared from ethyl chloroacetate (15 ml) and lithium bromide (2.21 g), and the reaction was carried out at an internal temperature of 115~130° C. for 18 hours. This reaction mixture was cooled to ≦70° C. and worked up as in Example 4 to provide ethyl 2-(7-chloro-2,4-dioxo-1,2,3,4-tetrahydroquinazolin-1-yl)acetate (13.66 g).

What is claimed is:

1. A process for producing a quinazoline derivative or a salt thereof comprising reacting:

a compound of the general formula:

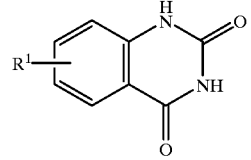

(II)

or a salt thereof, wherein $R^1$ is hydrogen or halogen, with a silylating agent, and further with a compound of the general formula (III):

Cl—A—$R^2$ (III)

or a salt thereof, wherein $R^2$ is carboxy or protected carboxy and A is lower alkylene,
in the presence of a catalyst selected from the group consisting of:
a compound of the general formula Br—Y—$R^3$ or a salt thereof, wherein $R^3$ is carboxy or protected carboxy and Y is lower alkylene; and
a compound of the general formula: Br—$R^4$ or a salt thereof, wherein $R^4$ is substituted or unsubstituted silyl;
optionally followed by desilylation, to provide a quinazoline derivative of the general formula:

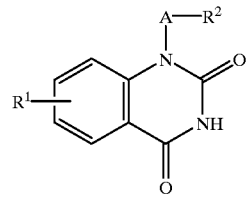

(I)

or a salt thereof,
wherein $R^1$, $R^2$ and A are each as defined above.

2. The process according to claim 1, wherein the reaction with compound (III) or its salt is carried out in the presence of a catalyst of the general formula:
Br—Y—$R^3$ or a salt thereof, wherein $R^3$ is carboxy or protected carboxy and Y is lower alkylene.

3. A process for producing a quinazoline derivative or a salt thereof comprising reacting:
a compound of the general formula:

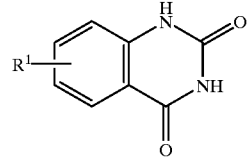

(II)

or a salt thereof, wherein $R^1$ is hydrogen or halogen, with a silylating agent, and further with a compound of the general formula (III):

Cl—A—$R^2$ (III)

or a salt thereof, wherein $R^2$ is carboxy or protected carboxy and A is lower alkylene, in a solvent having dielectric constant ∈ not less than 5, optionally followed by disilylation, to provide a quinazoline derivative of the general formula (I):

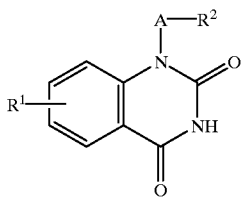

(I)

or a salt thereof, wherein $R^1$, $R^2$ and A are each as defined above.

4. A process for producing a quinazoline derivative or a salt thereof comprising reacting:
a compound of the general formula:

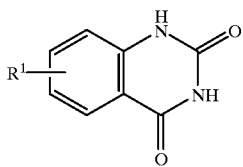

(II)

or a salt thereof, wherein $R^1$ is hydrogen or halogen, with a silylating agent, and further with a compound of the general formula (III):

 (III)

or a salt thereof, wherein $R^2$ is carboxy or protected carboxy and A is lower alkylene, in a solvent having dielectric constant $\in$ not less than 5, and
in the presence of a catalyst selected from the group consisting of:
a compound of the general formula:
Br—Y—$R^3$ or a salt thereof,
wherein $R^3$ is carboxy or protected carboxy and Y is lower alkylene;
a compound of the general formula:
Br—$R^4$ or a salt thereof, wherein $R^4$ is substituted or unsubstituted silyl;
and a compound of the general formula:
$MX^1$, wherein M is an alkali metal, and $X^1$ is bromo or iodo;
optionally followed by disilylation, to provide a quinazoline derivative of the general formula (I):

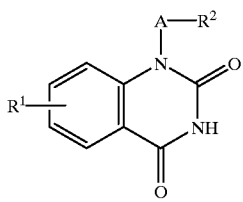

(I)

or a salt thereof, wherein $R^1$, $R^2$ and A are each as defined above.

5. The process according to claim 4, wherein the reaction with compound (III) or its salt is carried out in the presence of a catalyst selected from the group consisting of a compound of the general formula:
Br—Y—$R^3$ or a salt thereof, $R^3$ is carboxy or protected carboxy and Y is lower alkylene;
a compound of the general formula:
Br—$R^4$ or a salt thereof, wherein $R^4$ is substituted or unsubstituted silyl; and
a compound of the general formula:
$MX^1$, wherein M is an alkali metal, and $X^1$ is bromo.

6. The process according to claim 5, wherein the reaction with compound (III) or its salt is carried out in the presence of a catalyst selected from the group consisting of a compound of the general formula:
Br—Y—$R^3$ or a salt thereof, wherein $R^3$ is carboxy or protected carboxy and Y is lower alkylene, and
a compound of the general formula:
Br—$R^4$ or a salt thereof, wherein $R^4$ is substituted or unsubstituted silyl.

7. The process according to claim 6, wherein the reaction with compound (III) or its salt is carried out in the presence of a catalyst of the general formula:
Br—Y—$R^3$ or a salt thereof, wherein $R^3$ is carboxy or protected carboxy and Y is lower alkylene.

* * * * *